US007629121B2

(12) United States Patent
Srivastava et al.

(10) Patent No.: US 7,629,121 B2
(45) Date of Patent: Dec. 8, 2009

(54) NOTCH1 VARIANTS ASSOCIATED WITH CARDIOVASCULAR DISEASE

(75) Inventors: Deepak Srivastava, Dallas, TX (US); Vidu Garg, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 724 days.

(21) Appl. No.: 11/015,098

(22) Filed: Dec. 17, 2004

(65) Prior Publication Data

US 2006/0134645 A1 Jun. 22, 2006

(51) Int. Cl.
*C12Q 1/68* (2006.01)
*C07H 21/02* (2006.01)

(52) U.S. Cl. .......................................... 435/6; 536/23.1

(58) Field of Classification Search ....................... None
See application file for complete search history.

(56) References Cited

OTHER PUBLICATIONS

Hacker et al; Gut, 1997, vol. 40, pp. 623-627).*
Pennisi, Science, 1998; 281 (5384):1787-1789.*
Mohamed et al, Biophysical and Biochemical research communications, vol. 345, pp. 1460-1465, 2006.*
Rosenhek, Circulation, vol. 110, pp. 1291-1295, 2004.*
* cited by examiner

*Primary Examiner*—J D Schultz
*Assistant Examiner*—Katherine Salmon
(74) *Attorney, Agent, or Firm*—Richard Aron Osman

(57) ABSTRACT

Human individuals at increased risk for vascular pathology are identified by determining whether the individuals' genome comprises a Notch1 allele predetermined to be associated with an increased risk for vascular pathology. Notch1 alleles are identified as being associated with increased risk for vascular pathology by detecting the presence of a same Notch allele in a plurality of persons with increased risk for vascular pathology.

15 Claims, No Drawings

NOTCH1 VARIANTS ASSOCIATED WITH CARDIOVASCULAR DISEASE

This work was supported by National Institute of Health Grant Nos. RO1 HLDE62591-01 and K08-HD001382-04. The U.S. government may have rights in any patent issuing on this application.

FIELD OF THE INVENTION

The field of the invention is Notch1 mutations associated with congenital and adult cardiovascular disease.

BACKGROUND OF THE INVENTION

Bicuspid aortic valve (BAV) is the most common type of congenital heart anomaly with an estimated incidence of 1-2% (Hoffman and Kaplan, 2002). While the presence of only two aortic valve leaflets instead of three may not be recognized early in life, progressive dysfunction of the valve is common. Age-related calcification of the aortic valve results in stenosis and insufficiency in one-third of affected individuals and also causes an elevated risk for infective endocarditis (Ward, 2000; Fedak et al, 2002). Calcium deposits in the valve are associated with increased incidence of coronary artery calcification and are more prominent in the setting of increased serum lipids, hypertension, and diabetes (Roberts, 1986; Stewart et al, 1997; Palta et al, 2000; Walsh et al, 2004). Obstruction of blood flow and regurgitation caused by an improperly functioning aortic valve results in an increased workload on the left ventricle and ultimately heart failure. Incomplete leaflet separation between two of the three valve leaflets is the underlying developmental defect, but pathogenesis of the long-term calcification has remained a mystery.

There is abundant evidence suggesting a significant inherited component to the etiology of BAV (Cripe et al, 2004). Children with hypoplastic left heart syndrome (HLHS) represent the most severe type of aortic valve obstruction, which results in failure of left ventricular growth during fetal life. 15-20% of relatives of children with HLHS have BAV, often undiagnosed, suggesting a common genetic etiology with phenotypic heterogeneity for these cardiac malformations (Loffredo et al, 2004). In addition, the congenital heart disease (CHD) recurrence risk for parents of children with HLHS is 10-15%, compared to 3-5% for most other CHDs (Nora and Nora, 1988; Whittemore et al, 1994). Based on such observations, an oligogenic cause for BAV and HLHS with other environmental or stochastic influences has been proposed, however the gene(s) that might contribute are unknown (Lewin et al, 2004).

The Notch1 gene encodes a 2556 amino acid protein that contains an extracellular domain with 36 tandem epidermal growth factor (EGF)-like repeats, three cysteine-rich Notch/LIN-12 repeats and an intracellular domain with six ankryin repeats and a transactivation domain. The Notch signaling pathway is highly conserved and has been well described (Artavanis-Tsakonas et al, 1999). The Notch receptor interacts with two ligands, Delta and Jagged (or Serrate in Drosophila). Ligand binding results in at least two independent cleavages of the Notch receptor, first by a metalloprotease (Wen et al, 1997; Sotillos et al, 1997), then by presenilin (Struhl and Adachi, 1998; Struhl and Greenwald 1999). Clipping of the protein results in release of the Notch intracellular domain (Notch IC) from the membrane similar to that first described for sterol response binding protein (SREBP) (Sakai et al, 1996). Notch IC translocates to the nucleus where it interacts with Suppressor of Hairless (Su(H); RBPJk) to activate downstream target genes, including members of the Hairy (enhancer of split) family of transcriptional repressors. This pathway is involved in cell fate determination and differentiation during organogenesis throughout the embryo and is regulated by glycosylation of the extracellular EGF-like repeats (Haines and Irvine, 2003). Disruption of Notch1 in mice results in embryonic lethality by E9.5 from vascular defects (Swiatek et al, 1994) but recent studies suggest that Notch1 is involved in cardiac epithelial-mesenchymal transformation in frogs and zebrafish (Loomes et al, 2002; Timmerman et al, 2004).

Here, we show that mutations in the signaling and transcriptional regulator Notch1 cause developmental aortic valve anomalies and premature valve calcification in autosomal dominant human pedigrees. We also found a Notch1 single nucleotide polymorphism (SNP) that resulted in an R1280H substitution present in two percent of the general population and demonstrated that this SNP conferred a nearly fifty percent risk for aortic valve calcification. Furthermore, we show that Notch1 normally represses the activity of Runx2, a central transcriptional regulator of the osteoblast cell fate, and that Notch1 repression of Runx2 in the valve was likely through Hairy-related transcriptional repressors belonging to the Hrt family of basic helix-loop-helix proteins. These results indicate that Notch1 mutations cause an early developmental defect in the aortic valve and a later de-repression of calcium deposition that result in progressive aortic valve disease. Furthermore, population genetics of Notch1 polymorphisms revealed individuals at increased risk for premature vascular calcification, identifying a large number that would benefit from early diagnosis and prevention.

Relevant Literature

Tezuka, K. et al., (J Bone Miner Res 17:231-9, 2002) report stimulation of osteoblastic cell differentiation by Notch.

Sciaudone et al. (Endocrinology. 144:5631-9, 2003) report that Notch 1 can impair osteoblastic cell differentiation.

Rajamannan, N. M. et al. (Circulation 107, 2181-4, 2003) report that human aortic valve calcification is associated with an osteoblast phenotype.

Zamurovic, N., et al. (J Biol Chem. 279:37704-15, 2004) report coordinated activation of notch, Wnt, and transforming growth factor-beta signaling pathways in bone morphogenic protein 2-induced osteogenesis, and that Notch target gene Hey1 inhibits mineralization and Runx2 transcriptional activity.

Zayzafoon, M., et al. (J Biol Chem. 279:3662-70, 2004) report Notch signaling and ERK activation are important for the osteomimetic properties of prostate cancer bone metastatic cell lines.

SUMMARY OF THE INVENTION

A first aspect of the invention is a method of identifying a human individual for increased risk for vascular disease, the method comprising the step of:

(a) determining whether the individual's genome comprises a Notch1 allele predetermined to be associated with an increased risk for vascular disease, wherein the presence of the allele identifies the individual as at increased risk for vascular disease.

In one embodiment of the invention, the vascular disease is a vascular endothelium pathology, particularly calcification-associated vascular disease, and aortic valve pathologies, including aortic valve calcifications, malformations, malfunctions, stenosis or insufficiency, or endocarditis that occur as a result of such malformation or calcification.

In another embodiment, the allele comprises a single nucleotide polymorphism (SNP) selected from the group consisting of G1862A (R621H), C2542A (E848K), G2816A (R939Q), C3322T (R1108X), G3839A (R1280H), C4310T (A1437V), 4515Del (H1505del), G4826A (R1609H), C6817T (R2273C), and G6856A (V22861).

In another embodiment, the allele expresses as a transcript subject to nonsense mediated decay and causes a Notch1 haploinsufficiency.

In another embodiment, the allele encodes a variant sequence Notch1 protein.

In another embodiment, the vascular disease is aortic valve calcification and the allele comprises G3839A (R1280H).

In another embodiment, the determining step comprises detecting the allele using a method selected from the group consisting of: oligonucleotide microarray analysis, allele-specific hybridization, allele-specific PCR, and sequencing.

In another embodiment, the individual has a personal or family history of heart disease.

In another embodiment, the method further comprises step (b) prescribing the individual identified as being at increased risk for vascular pathology with therapy to prevent or slow progression of the pathology.

In another embodiment, the method further comprising step (b) treating the individual identified as being at increased risk for vascular pathology with therapy to prevent or slow progression of the pathology.

In another embodiment, the method further comprises step (b) prescribing the individual identified as being at increased risk for vascular pathology with therapy to prevent or slow progression of the pathology, wherein the therapy comprises taking a medication selected from the group consisting of digitalis, a diuretic, an anticoagulant, a beta-blocker, a calcium channel blocker, an ACE inhibitor, an antiarrhythmic, a RunX2 inhibitor (e.g. Parathyroid hormone-related peptide (PTHrP); see, e.g. Exp Cell Res. 2004 Sep. 10;299:128-36), a notch agonist (see, e.g. Zlobin A. et al., Curr. Pharm. Biotechnol. 1, 83-106, 2000), a statin, and an antibiotic.

In another embodiment, the method further comprises (b) treating the individual identified as being at increased risk for vascular pathology with therapy to prevent or slow progression of the pathology, wherein the therapy comprises taking a medication selected from the group consisting of digitalis, a diuretic, an anticoagulant, a beta-blocker, a calcium channel blocker, an ACE inhibitor, an antiarrhythmic, a RunX2 inhibitor, a notch agonist, a statin, and an antibiotic; and (c) detecting a resultant inhibition of vascular pathology.

A second aspect of the invention, is a method of identifying a Notch1 allele as being associated with increased risk for vascular pathology, the method comprising the step of (a) detecting the presence of a same Notch allele in a plurality of persons with increased risk for vascular pathology, wherein the selective presence of the allele in these persons identifies the allele as being associated with increased risk of vascular pathology.

In one embodiment of the invention, prior to (a), the persons are diagnosed as having heart disease and/or defects.

In another embodiment, the persons have family histories of heart disease.

In another embodiment, the allele expresses as a transcript subject to nonsense mediated decay and causes a Notch1 haploinsufficiency.

In another embodiment, the allele encodes a variant sequence Notch1 protein.

Another aspect of the invention is an isolated mutant human Notch1 polypeptide that differs from wild type human Notch1 polypeptide by a single amino acid substitution of R1280H.

Another aspect of the invention is an isolated antibody that specifically binds to a mutant human Notch1 protein and not to a wild-type Notch1 protein, wherein the mutant human Notch1 polypeptide differs from the wild type human Notch1 polypeptide by a single amino acid substitution of R1280H.

Other aspects of the invention include 1) an isolated recombinant polynucleotide that encodes a mutant human Notch1 polypeptide that differs from wild type human Notch1 polypeptide by a single amino acid substitution of R1280H; 2) an expression vector comprising the polynucleotide; and 3) a cell comprising the polynucleotide.

A final aspect of the invention is an isolated nucleic acid probe specifically hybridizable to a segment of a variant Notch1 DNA and not to a wild-type Notch1 DNA, wherein the variant Notch1 DNA comprises a SNP of G3839A (R1280H).

DETAILED DESCRIPTION OF EMBODIMENTS OF THE INVENTION

One aspect of the invention is a method of identifying a human individual for increased risk for vascular pathology the method comprising the step of (a) determining whether the individual's genome comprises a Notch1 allele predetermined to be associated with an increased risk for a vascular pathology, wherein the presence of the allele identifies the individual as at increased risk for vascular pathology.

The subject vascular diseases and pathologies are generally vascular endothelium pathologies, and include aortic valve pathologies and vascular calcification, including calcification of ascending and descending aorta and coronary vessels. Vascular endothelium pathologies, and aortic valve pathologies in particular, are readily ascertainable and well known in the art of cardiovascular disease (e.g. Otto, C M, Valvular Heart Disease, W. B. Saunders Co., $2^{nd}$ Ed. (2003) ISBN: 0721697879). In particular families, we have identified Notch alleles associated with an increased risk of numerous vascular pathologies associated with such Notch-1 alleles, including aortic valve calcifications, malformations, malfunctions, stenosis or insufficiency, or endocarditis that occur as a result of such malformations or calcifications.

We disclose a large number of exemplary Notch1 alleles predetermined to be associated with an increased risk for vascular pathology, and provide routine screening methods coupled with numerous working examples that enable one skilled in the art readily and without undue experimentation to characterize additional Notch 1 alleles as associated with an increased risk for vascular pathology. These screening methods require only routinely detecting the presence of a candidate Notch allele in a plurality of persons with increased risk for vascular pathology, wherein the selective presence of the allele in these persons identifies the allele as being associated with increased risk of vascular pathology.

Notch1 alleles associated with an increased risk for vascular pathology encode a variety of expression product variations, including amino acid deletions, insertions and substitutions, and protein truncations, particularly variations that result in haploinsuffiency. The subject alleles are conveniently described as SNPs of the wild-type human Notch1 gene. For example, Table A lists a number of exemplary Notch 1 SNPs associated with an increased risk for vascular pathology that we have identified in individuals with congenital cardiac malformations and various vascular pathologies.

The corresponding amino acid change and Notch1 domain affected are also indicated, demonstrating that variations associated with an increased risk for vascular pathology occur throughout both the intracellular and extracellular domains. Amino acid and nucleotide numbering used in Table A and throughout this disclosure is based on wild-type Notch1 sequences, e.g. published as GenBank Accession numbers NP_060087 and NM_017617, respectively.

TABLE A

| Amino Acid Change | Nucleotide Change | Notch Domain Affected |
|---|---|---|
| R621H | G1862A | EGF-like repeat 16 |
| E848K | G2542A | EGF-like repeat 22 |
| R939Q | G2816A | EGF-like repeat 24 |
| R1108X | C3322T | Truncation at EGF-like repeat 29 |
| R1280H | G3839A | EGF-like repeat 33 |
| A1437V | C4310T | Extracellular domain |
| H1505del | C4515del | Truncation at LIN/Notch domain 2 |
| R1609H | G4826A | Extracellular domain |
| R2273C | C6817T | Transactivation domain |
| V2286I | G6856A | Transactivation domain |

In specific embodiments of the invention, the allele encodes a variant sequence Notch1 protein, such as a Notch1 having any one of the amino acid substitutions listed in Table A. In more specific embodiments, the method comprises determining whether the individual's genome comprises a Notch1 allele that comprises an SNP selected from the group consisting of G1862A (R621H), C2542A (E848K), G2816A (R939Q), C3322T (R1108X), G3839A (R1280H), C4310T (A1437V), 4515Del (H1505del), G4826A (R1609H), C6817T (R2273C), and G6856A (V22861).

Preferred alleles occur at a populational frequency and provide an increased risk sufficient to warrant routine screening of at least selected at-risk groups. Such frequencies can range from 0.001% or 0.01% to 10% or more, depending on the increased risk, which typically ranges from 1% or 10%, to 50% or 90% or more. For example, as further described herein, we found that the Notch1 polymorphism G3839A (R1280H) occurs in 2% of the population and is associated with a nearly fifty percent risk of premature vascular calcification, warranting routine screening for this allele. Thus, in a further embodiment of the invention, the pathology is vascular calcification, particularly aortic valve calcification, and the allele comprises G3839A (R1280H).

In a further embodiment, the variant sequence Notch1 protein may be truncated. Because amino acid substitutions within the transactivation domain correlate with CHD and vascular pathology, carboxyl truncated Notch1 protein with at least a portion of the transactivation domain deleted also associate with increased risk for vascular pathology.

In another specific embodiment, the Notch1 allele expresses as a transcript subject to nonsense mediated decay (Frischmeyer et al, 2002) and causes a Notch1 haploinsufficiency. For example, both the C3322T (R1108X) and C4515del (H1505del) mutations generate truncated transcripts subject to nonsense-mediated decay.

Determining whether the individual's genome comprises a Notch1 allele predetermined to be associated with an increased risk for vascular pathology may be effected by a variety of established techniques, both directly and inferentially. For example, the Notch1 allele can be detected using any of the numerous genotyping methodologies known in the art (Shi, Am J Pharmacogenomics 2(3):197-205, 2002; Koch, Nature Reviews 3, 749-761, 2004). In one embodiment of the invention, the determining step comprises detecting the allele using a method selected from the group consisting of: oligonucleotide microarray analysis (Lipshutz, Nature Genet. 21 (Suppl. 1), 20-24, 1999; Wakai, Nucleic Acids Res. 32(18): e141, 2004), allele-specific hybridization (Bugawan et al., Tissue Antigens 44, 137-147, 1994; Gilles et al., Nature Biotechnol. 17, 365-370, 1999); allele-specific PCR (Saiki et al, Nature 324, 163-166, 1986; Butz et al, BMC Genet. 5(1):3 2004), and sequencing. In other embodiments, the determining step is effected inferentially, such as wherein information about the individual's genome and/or Notch allele(s) will have been previously obtained and recorded in a record, such as a medical record, and the determining step comprises reviewing the record to determine whether the individual's genome comprises a Notch1 allele predetermined to be associated with an increased risk for vascular pathology. In another embodiment, genetic information about the individual's relatives can be used to infer whether the individual's genome comprises a Notch1 allele associated with an increased risk for vascular pathology.

Another embodiment of the invention comprises prescribing the individual identified as being at increased risk for vascular pathology and/or treating the individual with therapy to prevent or slow progression of the pathology. Such therapies might include medications to control heart workload and/or limiting strenuous activity, such as lifting heavy objects. Exemplary such medications include digitalis, to reduce the heart's workload and ease symptoms; diuretics, to lower salt and fluid levels in the body, lowering blood pressure; anticoagulant medicines, to prevent blood clots; beta-blockers, to control heart rate and lower blood pressure; calcium channel blockers, to affect the contractions of muscle tissue in the heart and lower blood pressure; ACE inhibitors, to widen blood vessels and lower blood pressure; antiarrhythmic medications, to normalize irregular heart rhythms (e.g. atrial fibrillation) caused by regurgitation; RunX2 inhibitors, to prevent expression of transcripts involved in osteoblast differentiation and mineralization; and statins to slow aortic valve calcium accumulation (Resnekov et al, Circulation 110: 1291-5, 2004). Patients with heart valve disease are also at increased risk for bacterial endocarditis and may be treated with prophylactic administration of antibiotics prior to dental and other surgical or medical procedures that might introduce bacteria into the bloodstream. Thus, in a further embodiment, the method further comprises step (b) prescribing the individual identified as being at increased risk for vascular pathology with therapy to prevent or slow progression of the pathology, wherein the therapy comprises taking a medication selected from the group consisting of digitalis, a diuretic, an anticoagulant, a beta-blocker, a calcium channel blocker, an ACE inhibitor, an antiarrhythmic, a RunX2 inhibitor, a notch agonist, a statin, and an antibiotic. In a further embodiment, individuals treated with the therapy are subsequently followed-up for detection of a resultant inhibition of vascular pathology. For example, electron beam computed tomography (EBCT) can be used to detect inhibition in vascular calcification, for example, by detecting a reduction in valve calcification or a decreased rate of valve calcification (Jain et al, 2004).

Another aspect of the invention is a method of identifying a Notch1 allele as being associated with increased risk for a vascular pathology, the method comprising the step of detecting the presence of a same Notch allele in a plurality of persons with increased risk for a vascular pathology, wherein the selective presence of the allele in these persons identifies the allele as being associated with increased risk of vascular pathology. An allele is selectively present in persons having increased risk for vascular pathology, if the same allele is significantly less prevalent in a control population of individuals that has no increased risk of vascular pathology. Persons having increased risk for vascular pathology include persons with a personal history of heart disease (e.g. previously diagnosed as having heart disease and/or defects, such as aortic valve calcification or BAV), persons having a family history of heart disease, and/or persons having other known risk factors for heart disease. In one embodiment, the allele detected expresses as a transcript subject to nonsense mediated decay and causes a Notch1 haploinsufficiency. In another embodiment, the allele detected encodes a variant sequence Notch1 protein, for example, having an amino acid substitution or truncation.

The invention provides isolated human Notch1 polypeptides associated with increased risk for vascular disease, including variants that differ from wild type human Notch1 polypeptide by a single amino acid substitution listed in Table A, such as R1280H. These polypeptides have utility in binding and other Notch functional assays to identify inhibitors of vascular calcification caused by these variant Notch1 proteins.

The subject Notch1 polypeptides can also be used to generate antibodies that specifically bind to the variant Notch1 proteins and not to wild-type Notch1 protein, particularly wherein the mutant human Notch1 polypeptide differs from the wild type human Notch1 polypeptide by a single amino acid substitution, such as R1280H. For example, an immunogenic fragment of the mutant Notch1 polypeptide comprising the R1280H point mutation can be used to generate the antibodies, such as a fragment that consists of the EGF-like repeat 33 domain which spans amino acids 1268-1306. Smaller immunogenic fragments (e.g. 10-30 amino acids) within this EGF-like repeat domain can also be used. The antibodies can be used to detect the presence of a variant Notch1 polypeptide in a patient sample, e.g. using immunohistochemistry or ELISA, and thus can be used in assays to diagnose a human individual for vascular pathology.

The subject Notch1 polypeptides and fragments can be expressed from recombinant cells and purified using known methods. Thus, one aspect of the invention is an isolated recombinant polynucleotide that encodes a subject human Notch1 polypeptide, particularly one that differs from wild type human Notch1 polypeptide by a single amino acid substitution listed in Table A, such as R1280H. Further aspects of the invention include expression vectors and cells comprising the recombinant polynucleotide. Suitable expression vectors and cells that can be used to express mutant Notch1 are known in the art. In one embodiment, preferred cell lines are those used for studying osteoblast mineralization such as C4-2B cells (Tezuka K., et al, 2002) and MC353 cells (Sciaudone M., et al, 2003).

The invention also provides an isolated nucleic acid probe specifically hybridizable to a segment of a subject variant Notch-1 DNA and not to a wild-type Notch-1 DNA, particularly wherein the variant Notch-1 DNA comprises a SNP listed in Table A, such as G3839A (R1280H). The probe can be of any length appropriate for its intended use. Typically, the probes are 12 or more nucleotides in length. The probes can be included as a component of a genotyping kit, such as an oligonucleotide array, and may be accompanied with instructional material with directions on how to use the kit to identify human individuals for increased risk for vascular disease.

EXAMPLES

Aortic valve calcification is the third leading cause of heart disease in adults. The incidence increases with age and is often associated with a developmental anomaly of the aortic valve. Despite the incidence, neither the cause of aortic valve anomalies nor the mechanisms that result in calcification are known. Here, we show that isolated aortic valve malformations and premature valve calcification in a large pedigree were linked to chromosome 9q34-35. A heterozygous R1108X nonsense mutation of NOTCH1 was found in all available affected family members but not in control individuals. We identified a second family with a frame-shift mutation of NOTCH1 (H1505del) that segregated with vascular disease, indicating haploinsufficiency of NOTCH1 in both families. We found that an R1280H NOTCH1 sequence variation, present in two percent of the general population, conferred a nearly fifty percent risk for aortic valve calcification. Consistent with the phenotype in humans, we found that Notch1 inhibited the activity of Runx2, a critical osteoblast-promoting transcription factor. These data demonstrate the first genetic etiology of aortic valve disease in humans and reveal an essential role for NOTCH1 in suppressing age-related ectopic calcification.

Identification of Notch1 Mutations in Familial Heart Disease. We identified a large family (Family A) spanning five generations in which eleven individuals had CHD. Clinical evaluations regarding their medical history that included cardiac and non-cardiac studies were reviewed for all available family members, and demonstrated an autosomal dominant pattern of CHD inheritance. Nine of the affected family members had aortic valve disease. In eight of these cases, an abnormal aortic valve was the only cardiac malformation. Five of these eight had BAV and the remaining three developed aortic stenosis. A single individual had an associated abnormal mitral valve, resulting in mitral valve stenosis, and a ventricular septal defect (VSD) while an isolated VSD and tetralogy of Fallot with a bicuspid pulmonic valve were identified in two other affected family members. Five family members have thus far required valve replacement. There were no cardiac conduction abnormalities or other birth defects identified. Detailed clinical phenotype information for this kindred is shown in Table 1A. The first column in each of Tables 1A and 1B indicates the generation number for each family member (i.e. I- for $1^{st}$ generation, II- for $2^{nd}$ generation, etc.). The following abbreviations are used in Tables 1A and 1B: AS=aortic stenosis; AI=aortic insufficiency; AVR=aortic valve replacement; AoR=aortic root replacement; AA=ascending aortic aneurysm; BAV=bicuspid aortic valve; CHD=congenital heart disease; DORV=double outlet right ventricle; HLV=hypoplastic left ventricle; MA=mitral atresia; MVR=mitral valve replacement; MS=mitral stenosis; MV=mitral valve; PM=pacemaker; PDA=patent ductus arteriosus; TOF=tetralogy of Fallot; VSD=ventricular septal defect; CA=cancer; CVA=cerebrovascular accident; HTN=hypertension; MI=myocardial infarction; U=unknown.

TABLE 1A

| | CHD | Severity | Aortic Valve Morphology | Surgery | Aortic Valve Replacement | Other anomalies/ disease | Cause of Death |
|---|---|---|---|---|---|---|---|
| I-1 | U | | U | – | | No heart disease | Colon CA (66yo) |
| I-2 | U | | U | – | | | MI (62yo) |
| II-1 | AS, AI, dilated asc aorta | Severe | Three leaflet | + | + (65yo) | HTN, hyperlipidemi a, CVA, breast CA | |
| II-2 | AS | U | U | + | + (76yo) | | CVA after AVR |
| III-1 | Normal | | | | | | |
| III-2 | Normal | | | | | | |
| III-3 | Abnormal AV | U | Three leaflet | – | – | Uterine CA | Eisenmenger |
| III-4 | VSD | | U | – | – | Scoliosis | Sudden death |
| III-5 | AS, dilated asc aorta | Severe | BAV | + | + (26yo) | Retinal embolism | |
| III-6 | AI | Severe | BAV | + | + (33yo) | HTN, depression | |
| III-7 | Normal | | | | | | |
| III-8 | AI | Mild | BAV | – | | | MVA |
| III-9 | U | | U | – | | | After surgery |
| IV-1 | TOF, bicuspid PV | | Three leaflet | + | – | None | |
| IV-2 | AS | Mild | Three leaflet | – | – | Seizure disorder | |
| IV-3 | U | | | – | | | |
| IV-4 | VSD, MS, parachute MV | | BAV | + | – | s/p VSD closure; s/p MVR | |
| V-1 | AS, dilated Sc aorta | Mild | BAV | – | – | | |
| V-2 | Normal | | | | | | |

We performed a genome-wide scan of available family members that revealed linkage of the CHD phenotype to a single locus on chromosome 9q34 between D9S158 and D9S1838 (LOD score=3.5, θ=0), spanning approximately 1.5 megabases (~2 cM). Examination of genes in this interval revealed the presence of NOTCH1, encoding a transmembrane receptor that functions in a highly conserved intracellular signaling pathway involved in cellular differentiation and lateral inhibition (Artavanis-Tsakonas et al, 1999). Direct sequencing of NOTCH1 in an affected patient revealed a C-to-T transition of nucleotide 3322 that predicted the substitution of a premature stop codon instead of an arginine residue at position 1108. All available affected individuals that were clinically evaluated had the R1108Stop mutation, indicating autosomal dominant inheritance of the disease phenotype with complete penetrance. The mutant allele was not detected in unaffected family members or in 1137 unrelated individuals of diverse ethnicity, making it unlikely that R1108Stop represented a rare polymorphism. In the proband, we sequenced 100 additional regulatory genes essential for, or expressed during cardiac development but failed to identify other linked mutations, consistent with a monogenic etiology.

By direct sequencing of NOTCH1 in a smaller unrelated family (Family B) with aortic valve disease, we found a second NOTCH1 mutation that segregated with three affected family members. In this pedigree, all affected family members had BAV. The proband had BAV associated with complex congenital heart disease consisting of mitral atresia, hypoplastic left ventricle and double-outlet right ventricle (aorta and pulmonary artery arising from the right ventricle), while his sibling and mother had BAV with associated aortic stenosis. Family member II-2 did not have aortic valve disease but did have an ascending aortic aneurysm. Detailed clinical phenotype information for this kindred is shown in Table 1B.

TABLE 1B

| | CHD | Severity | Aortic Valve Morphology | Surgery | Aortic Valve Replacement | Other anomalies/ disease | Cause of Death |
|---|---|---|---|---|---|---|---|
| I-1 | U | | U | – | | | |
| I-2 | U | | U | – | | | |
| II-1 | AS | Severe | BAV | + | Yes | AA, s/p AoR | |
| II-2 | Normal | | Three leaflet | + | No) | AA, s/p AoR, s/p PM | |

TABLE 1B-continued

| | CHD | Severity | Aortic Valve Morphology | Surgery | Aortic Valve Replacement | Other anomalies/ disease | Cause of Death |
|---|---|---|---|---|---|---|---|
| III-1 | MA, HLV, DORVI | | BAV | + | | Palliative surgery | |
| III-2 | AS | Severe | BAV | + | Yes | | |
| III-3 | Normal | | | | | | |
| III-4 | Normal | | | | | | |

A single base pair deletion of nucleotide 4515 segregated with aortic valve disease in this family and resulted in a frameshift mutation (H1505del) that predicted a premature a severely altered protein containing 74 incorrect amino acids at the C-terminus followed by stop codon. Both of these identified mutations in NOTCH1 generate truncated transcripts that likely undergo nonsense mediated decay and together provide compelling genetic evidence that NOTCH1 haploinsufficiency results in human CHD (Frischmeyer et al, 2002).

Notch1 transcripts are enriched in the developing aortic valve. To determine if Notch1 expression during development was consistent with the predominant phenotype in humans, we performed in situ hybridization at multiple stages during cardiogenesis, focusing on Notch1 transcripts in the cardiac valves and their precursors. At mouse embryonic day (E) 11.5, we found enrichment of Notch1 mRNA transcripts expression in the outflow tract mesenchyme, which gives rise to the valves, in addition to the endocardium. At the time of septation of the common arterial trunk (E13.5), high levels of Notch1 expression were observed in not only in the endothelial layer but also in the mesenchyme of the aortic valve leaflets. Together, these studies indicate Notch signaling in the morphological development of the aortic valve as described in the families above.

Notch1 Sequence Variations in CHD. In order to determine if mutations in NOTCH1 were present in other individuals with CHD, we sequenced an additional fifty-three familial and sporadic cases of cardiac malformations similar to those identified in the families described above. Sequence variations that resulted in non-synonymous amino acid changes were studied further. The incidence of these sequence variations in a population of random ethnically diverse individuals was determined. Each of these sequence variations resulted in mutation of a conserved amino acid residue. Table 2 summarizes the data.

TABLE 2

| Amino Acid Change | Nucleotide Change | Frequency in CHD | Frequency in Control | P Value |
|---|---|---|---|---|
| R621H | G1862A | 1/53 (1.9%) | 4/3439 (0.12%) | <0.001 |
| R1280H | G3839A | 2/53 (3.8%) | 78/3429 (2.3%) | NS |
| R2273C | C6817T | 1/53 (1.9%) | 0/1138 (0%) | <0.001 |

One of the variations was a heterozygous C-to-T transition of nucleotide 6817 that was not present in any of the 1138 controls. This mutation predicted the amino acid substitution of an arginine residue with a cysteine at codon 2273 (R2273C) and occurred in a patient with non-familial complex CHD consisting of a stenotic pulmonary valve and malalignment of the aorta with the ventricular chambers. Screening of family members who were examined by echocardiography demonstrated that the SNP was inherited from an apparently unaffected parent and was likely incompletely penetrant. This arginine is conserved in humans, mice and zebrafish and lies within the intracellular transactivation domain of NOTCH1, which functions as a nuclear transcription factor.

The G1862A (R621H) and G3839A (R1280H) non-synonomous sequence variations in NOTCH1 identified in our patient population were found with varying frequencies in the control population. Only R621H demonstrated a statistically significant difference in incidence compared to the 3439 controls (p value<0.001, Chi-square test), with four out of 3,439 harboring the R621H mutation. Mutation of this highly conserved residue was identified in a familial case of BAV (Family C) but did not segregate with the disease making it unlikely that it was associated with the cardiac malformation, although it confers risk. The R1280H SNP occurred in a familial and non-familial case of cardiac disease. It was present in a familial case of BAV and segregated with disease and also in a non-familial case of HLHS consisting of aortic and mitral atresia. Screening of our control population demonstrated that it was an uncommon polymorphism present in approximately 2% of the population that conformed to Hardy-Weinberg equilibrium with the identification of 2 homozygous individuals and 76 heterozygote carriers.

Notch1 R1280H is a Risk Factor for Aortic Valve Calcification. Given that BAV is present in 1-2% of all individuals and is a risk factor for aortic valve calcification, we asked if any of the NOTCH1 polymorphisms were associated with aortic valve calcification. The nearly 3500 "control" individuals described above were part of a random population in the Dallas Heart Study that was also phenotyped by electron beam computed tomography (EBCT), a sensitive test for calcium deposits (Jain et al, 2004). Upon interrogation of the EBCT database, we found that the more common SNP, R1280H, which occurred in 2% of the population, was associated with a nearly fifty percent risk of premature aortic valve calcification. Individuals from the Dallas Heart Study not carrying a NOTCH1 SNP and matched for age, sex, body mass index (BMI), lipid profile and tobacco use had only a 28% incidence of calcium deposits detectable by EBCT. Thus, the presence of the R1280H NOTCH1 SNP was an independent predictor for aortic valve calcification (odds ratio=2.2, 95% confidence interval: 1.03-4.68). In summary, our data indicate that the NOTCH1 R1280H allele is an independent risk factor for aortic valve calcification.

Expression of osteopontin has been reported in human calcific aortic stenosis (O'Brien et al, 1995, Rajamannan et al, 2003). Osteopontin and many other osteoblast-specific genes are transcriptionally regulated through upstream cis elements that bind to the transcription factor, Runx2, also known as Cbfa (Ducy et al, 1997). Runx2 can physically interact with the hairy protein, HES1, which represses Runx2's transcriptional activity (McLarren et al, 2000). We therefore investigated whether the cardiac family of hairy-related transcriptional repressors, Hrt1 and Hrt2, which we previously showed were activated by Notch1, might be expressed in the aortic valve and could function as repressors of Runx2 (Nakagawa et al, 2000). We found that Hrt1 and Hrt2 were indeed expressed in the endocardial lining of the aortic valve at E17.5 by in situ hybridization. In addition, both had varying levels of expression in the aortic smooth muscle, which is a common site of vascular calcification in disease states. Consistent with Hrt repression of Runx2, co-transfection of Hrt1 and Hrt2 resulted in repression of Runx2-induced activation of luciferase through a multimerized Runx2-binding cis element upstream of osteopontin. As predicted, the intracellular domain of Notch1 was sufficient to repress Runx2 responsive transactivation. Using a series of Hrt2 truncation mutants, we found that the basic helix-loop-helix (bHLH) domain of Hrt2 was necessary for full Hrt2-mediated repression of Runx2. In summary, our data indicate a pathway in which Notch1 represses Runx2 dependent osteoblastic gene expression via Hrt1 and Hrt2 in the aortic valve.

Discussion & Methods. Our discovery of NOTCH1 haploinsufficiency associated with vascular disease and premature calcification represents the first demonstration of NOTCH1 mutations in human disease. It is interesting that mutations in the NOTCH1 ligand JAGGED1 cause the much broader and distinct phenotype of Alagille syndrome (Li et al, 1997; Oda et al, 1997). This could be related to the presence of redundancy among NOTCH receptors or to the proposed cell-autonomous intracellular signaling role of JAGGED1, which would affect a completely distinct population of cells. In either case, the families reported here have not only led to an understanding of the cause of a human developmental malformation (BAV) present in one-two percent of the population, but have also revealed a mechanism through which BAVs may become calcified. Most remarkably, a NOTCH1 polymorphism that is present in 2% of the population has a fifty percent predictive value for premature aortic valve calcification, indicating that nearly 1% of the population can be identified as at risk by this single SNP. Preventive approaches such as aggressive management of serum lipids, hypertension and diabetes in those with NOTCH1 SNPs can delay onset of age-related calcific valve disease. Targeting the NOTCH1 pathway directly for pharmacologic intervention allows for more precise therapy of calcific disease.

Clinical phenotype evaluation and DNA collection: The CHD families and individuals were ascertained for genetic linkage analyses at Children's Medical Center Dallas (University of Texas Southwestern Medical Center), University of California, San Diego and University of Ottawa. Clinical evaluations and genetic studies were performed in accordance with human subject guidelines after informed consent according to the protocol approved by the individual Institutional Review Boards. Family members were studied by history, physical examination, 12-lead electrocardiogram, and echocardiography. Available medical records were reviewed for individuals who had expired. Genomic DNA was extracted from peripheral lymphocytes for genetic analyses. The screening population comprised 53 individuals with a CHD phenotype. The phenotypes were distributed into 21 familial cases of left-sided CHD (BAV, aortic stenosis, aortic coarctation, and HLHS), 24 cases with non-familial left-sided CHD, and 8 cases with tetralogy of Fallot or double outlet right ventricle (DORV).

Genetic linkage analysis. An autosomal-genome linkage analysis was performed using 372 polymorphic DNA markers at ~10 cM intervals (ABI Mapping Set v2.5). Markers were genotyped in all family members as previously described (Garcia et al, 2001). Linkage analysis was performed using GENEHUNTER (Kruglyak, et al, 1996).

Identification of NOTCH1 mutations: All exons of the NOTCH1 gene were sequenced in both directions to search for sequence variations in the proband of Families A and B and in the additional 53 individuals. The exons containing the R1108X and H1505del mutations were amplified by PCR for each of respective additional family members and sequenced in both directions. For families C, D, and F, a similar analysis was performed to determine if additional family members harbored the G1862A (R621H), G3839A (R1280H), and C6817T (R2273C) polymorphisms, respectively. PCR amplification was performed with the BD Biosciences Advantage GC Genomic PCR kit per the manufacturer instructions with an annealing temperature of 60° C. for these reactions.

Radioactive section in situ hybridization: 35S-labeled antisense riboprobes were synthesized with T7 RNA polymerase (MAXIScript, Ambion Inc, Austin, Tex.) from 400 base pair partial mouse Notch1 cDNA or plasmids encoding Hrt1 and Hrt2 (Nakagawa et al, 1999). Using these riboprobes, radioactive section in situ hybridization was performed on paraffin embedded sections of E11.5 and E13 and E17.5 mouse embryos as previously described (Garg et al, 2001).

Allelic Discrimination Assays: Large scale screening of identified human NOTCH1 nucleotide polymorphisms was performed using Allelic Discrimination assays using the ABI Prism 7900 HT Sequence Detection System with TaqMan probes according to manufacturer instructions (Livak, 1999). The DNA was obtained from individuals who participated in the Dallas Heart Study (Jain et al, 2004).

Electron bean computed tomography (EBCT) protocol and aortic root calcification: Electron beam computed tomography image acquisition and analysis was performed as previously described (Jain et al., 2004). The region of the aortic annulus to the sinotubular junction was evaluated. A focus was defined as a region of three or more contiguous voxels within a computed tomography(CT) number>130 HU. The voxel size was 0.586×586×3 mm (field of view 30 cm, matrix 512, 3-mm slice) so that three voxels would be a volume of 3.08 mm. Scans were read by a single individual and only the foci within the aortic annulus and root were scored. Results were expressed in Agatston U (Agatson AS, JACC, 1990) and the mean of the two scores was used as the final aortic calcification score. Individuals with a mean EBCT score of>10 Agatson U were classified as AVC positive.

Luciferase Assays: Cos7 cells were transfected using Fugene 6 (Roche) according to manufacturer instructions. The reporter plasmid (250 ng), p6OSE2 luciferase (Ducy et al, 1995), and CMV β-galactosidase expression plasmid (50 ng), to control for transfection efficiency, were transfected along with Runx2 expression plasmid (100 ng) and varying amounts of Hrt1, Hrt2, Notch1 intracellular domain and Hrt2 deletion expression plasmids. Hrt2 deletion constructs were generated as previously described (Kathiriya et al, 2004). Immunoblots were used to verify appropriate protein expression. Luciferase activity was measured 48 hours after transient transfection as previously described (Garg et al, 2003), and was normalized to LacZ expression to generate relative luciferase activity. At least three independent experiments were performed in duplicate.

Statistical Analysis: The Dallas Heart Study has been previously described (Jain et al, 2004). Chi-square test was used to compare associations between categorical variables. Student t test was used to compare means of continuous variables. For case control studies, odds ratios were calculated to estimate the risk for aortic valve calcification with the NOTCH1 R1280H allele. p values of ≦0.05 were considered statistically significant.

LITERATURE

1. Agatston, A S et al. Quantification of coronary artery calcium using ultrafast computed tomography. J Am Coll Cardiol 15, 827-32 (1990).
2. Artavanis-Tsakonas, S., Rand, M. D. & Lake, R. J. Notch signaling: cell fate control and signal integration in development. Science 284, 770-6 (1999).
3. Cripe, L., Andelfinger, G., Martin, L. J., Shooner, K. & Benson, D. W. Bicuspid aortic valve is heritable. J Am Coll Cardiol 44, 138-43 (2004).
4. Ducy, P., Zhang, R., Geoffroy, V., Ridall, A. L. & Karsenty, G. Osf2/Cbfa1: a transcriptional activator of osteoblast differentiation. Cell 89, 747-54 (1997).
5. Fedak, P. W. et al. Clinical and pathophysiological implications of a bicuspid aortic valve. Circulation 106, 900-4 (2002).
6. Frischmeyer, P. A. et al. An mRNA surveillance mechanism that eliminates transcripts lacking termination codons. Science 295, 2258-61 (2002).
7. Garcia, C. K. et al. Autosomal recessive hypercholesterolemia caused by mutations in a putative LDL receptor adaptor protein. Science 292, 1394-8 (2001).
8. Garg, V. et al. Tbx1, a DiGeorge syndrome candidate gene, is regulated by sonic hedgehog during pharyngeal arch development. Dev Biol 235, 62-73 (2001).
9. Garg, V. et al. GATA4 mutations cause human congenital heart defects and reveal an interaction with TBX5. Nature 424, 443-7 (2003).
10. Haines, N. & Irvine, K. D. Glycosylation regulates Notch signalling. Nat Rev Mol Cell Biol 4, 786-97 (2003).
11. Hoffman, J. I. & Kaplan, S. The incidence of congenital heart disease. J Am Coll Cardiol 39, 1890-900 (2002).
12. Jain, et al. African Americans and Caucasians Have a Similar Prevalence of Coronary Calcium in the Dallas Heart Study. J Am Coll Cardiol 44, 1011-7 (2004).
13. Kathiriya, I. S., et al. Hairy-related transcriptional factors inhibit GATA-dependent cardiac gene expression through a signal-responsive mechanism. J Biol Chem (2004).
14. Kruglyak, et al. Parametric and nonparametric linkage analysis: a unified multipoint approach. Am J Hum Genet 58, 1347-63 (1996).
15. Lewin, M. B. et al. Echocardiographic evaluation of asymptomatic parental and sibling cardiovascular anomalies associated with congenital left ventricular outflow tract lesions. Pediatrics 114, 691-6 (2004).
16. Li, L. et al. Alagille syndrome is caused by mutations in human Jagged1, which encodes a ligand for Notch1. Nat Genet 16, 243-51 (1997).
17. Livak, K. J. Allelic discrimination using fluorogenic probes and the 5' nuclease assay. Genet Anal 14, 143-9 (1999).
18. Loffredo, C. A. et al. Prevalence of congenital cardiovascular malformations among relatives of infants with hypoplastic left heart, coarctation of the aorta, and d-transposition of the great arteries. Am J Med Genet 124A, 225-30 (2004).
19. Loomes, K. M. et al. Characterization of Notch receptor expression in the developing mammalian heart and liver. Am J Med Genet 112, 181-9 (2002).
20. McLarren, K. W. et al. The mammalian basic helix loop helix protein HES-1 binds to and modulates the transactivating function of the runt-related factor Cbfa1. J Biol Chem 275, 530-8 (2000).
21. Nakagawa, O., Nakagawa, M., Richardson, J. A., Olson, E. N. & Srivastava, D. HRT1, HRT2, and HRT3: a new subclass of bHLH transcription factors marking specific cardiac, somitic, and pharyngeal arch segments. Dev Biol 216, 72-84 (1999).
22. Nakagawa, O. et al. Members of the HRT family of basic helix-loop-helix proteins act as transcriptional repressors downstream of Notch signaling. Proc Natl Acad Sci U S A 97, 1365560 (2000).
23. Nora, J. J. & Nora, A. H. Familial risk of congenital heart defect. Am J Med Genet 29, 231, 233 (1988).
24. O'Brien, K. D. et al. Osteopontin is expressed in human aortic valvular lesions. Circulation 92, 2163-8 (1995).
25. Oda, T. et al. Mutations in the human Jagged1 gene are responsible for Alagille syndrome. Nat Genet 16, 235-42 (1997).
26. Palta, et al. New insights into the progression of aortic stenosis: implications for secondary prevention. Circulation 101, 2497-502 (2000).
27. Rajamannan, N. M. et al. Human aortic valve calcification is associated with an osteoblast phenotype. Circulation 107, 2181-4 (2003).
28. Roberts, W. C. The senile cardiac calcification syndrome. Am J Cardiol 58, 572-4 (1986).
29. Sakai, J. et al. Sterol-regulated release of SREBP-2 from cell membranes requires two sequential cleavages, one within a transmembrane segment. Cell 85, 1037-46 (1996).
30. Sotillos, S., Roch, F. & Campuzano, S. The metalloprotease-disintegrin Kuzbanian participates in Notch activation during growth and patterning of Drosophila imaginal discs. Development 124, 4769-79 (1997).
31. Srivastava, D. & Olson, E. N. A genetic blueprint for cardiac development. Nature 407, 221-6 (2000).
32. Stewart, B. F. et al. Clinical factors associated with calcific aortic valve disease. Cardiovascular Health Study. J Am Coll Cardiol 29, 630-4 (1997).
33. Struhl, G. & Adachi, A. Nuclear access and action of notch in vivo. Cell 93, 649-60 (1998).
34. Struhl, G. & Greenwald, I. Presenilin is required for activity and nuclear access of Notch in Drosophila. Nature 398, 522-5 (1999).
35. Swiatek, et al. Notch1 is essential for postimplantation development in mice. Genes Dev 8, 707-19 (1994).
36. Timmerman, L. A. et al. Notch promotes epithelial-mesenchymal transition during cardiac development and oncogenic transformation. Genes Dev 18, 99-115 (2004).
37. Walsh, C. R. et al. Association of aortic valve calcium detected by electron beam computed tomography with echocardiographic aortic valve disease and with calcium deposits in the coronary arteries and thoracic aorta. Am J Cardiol 93, 421-5 (2004).
38. Ward, C. Clinical significance of the bicuspid aortic valve. Heart 83, 81-5 (2000).
39. Wen, C., Metzstein, M. M. & Greenwald, I. SUP-17, a *Caenorhabditis elegans* ADAM protein related to Drosophila KUZBANIAN, and its role in LIN-12/NOTCH signalling. Development 124, 4759-67 (1997).
40. Whittemore, R., Wells, J. A. & Castellsague, X. A second-generation study of 427 probands with congenital heart defects and their 837 children. J Am Coll Cardiol 23, 1459-67 (1994).

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of identifying a human individual for increased risk for vascular pathology the method comprising the step of:

(a) determining whether the individual's genome comprises a Notch1 single-nucleotide polymorphism (SNP) allele causing Notch 1 haploinsufficiency and predetermined to be associated with an increased risk for vascular pathology, wherein the presence of the allele identifies the individual as at increased risk for vascular pathology, wherein the determining step comprises detecting the allele, wherein the SNP is selected from the group consisting of G1862A (R621H), C2542A (E848K), G2816A (R939Q), C3322T (R1108X), G3839A (R1280H), C4310T (A1437V), 4515Del (H1505del), G4826A (R1609H), C6817T (R2273C), and G6856A (V22861).

2. The method of claim 1 wherein the pathology comprises vascular calcification.

3. The method of claim 1 wherein the allele expresses as a transcript subject to nonsense mediated decay.

4. The method of claim 1 wherein the allele encodes a variant sequence Notch 1 protein.

5. The method of claim 1 wherein the pathology is aortic valve calcification and the SNP is G3839A (R1280H).

6. The method of claim 1 wherein the determining step comprises detecting the allele using a method selected from the group consisting of: oligonucleotide microarray analysis allele-specific hybridization, allele-specific PCR, and sequencing.

7. The method of claim 1 wherein the individual has a personal or family history of heart disease.

8. The method of claim 1, wherein the SNP is selected from the group consisting of G3839A (R1280H), G1862A (R621H), and C6817T (R2273C).

9. The method of claim 1, wherein the SNP is G1862A (R621H).

10. The method of claim 1, wherein the SNP is C6817T (R2273C).

11. The method of claim 1 wherein the pathology is aortic valve calcification.

12. The method of claim 1 wherein the pathology is aortic valve calcification, and the SNP is selected from the group consisting of G3839A (R1280H), G1862A (R621H), and C6817T (R2273C).

13. The method of claim 1 wherein the pathology is aortic valve calcification, wherein the determining step comprises detecting the allele using a method selected from the group consisting of: oligonucleotide microarray analysis, allele-specific hybridization, allele-specific PCR, and sequencing.

14. The method of claim 5 wherein the determining step comprises detecting the allele using a method selected from the group consisting of: oligonucleotide microarray analysis, allele-specific hybridization, allele-specific PCR, and sequencing.

15. The method of claim 12 wherein the determining step comprises detecting the allele using a method selected from the group consisting of: oligonucleotide microarray analysis, allele-specific hybridization, allele-specific PCR, and sequencing.

* * * * *